United States Patent [19]

Bröker et al.

[11] Patent Number: 5,369,029
[45] Date of Patent: Nov. 29, 1994

[54] **METHOD FOR DEGRADING NUCLEIC ACIDS IN WASTE FERMENTATION SOLUTIONS WITH *PAECILOMYCES LILACINUS***

[75] Inventors: Michael Bröker; Mathias Fibi, both of Marburg, Germany

[73] Assignee: Behringwerke Aktiengesellschaft, Marburg, Germany

[21] Appl. No.: 41,351

[22] Filed: Apr. 1, 1993

Related U.S. Application Data

[63] Continuation of Ser. No. 619,449, Nov. 29, 1990, abandoned.

[30] Foreign Application Priority Data

Dec. 1, 1989 [DE] Germany ............... 3939771

[51] Int. Cl.$^5$ .............. C12N 1/08; C12N 9/16; C12N 1/00
[52] U.S. Cl. ................. 435/262.5; 435/932; 435/196
[58] Field of Search .............. 435/262.5, 196, 822, 435/270, 932

[56] References Cited

U.S. PATENT DOCUMENTS

| | | | |
|---|---|---|---|
| 3,887,431 | 6/1975 | Robbins et al. | 530/371 |
| 3,966,543 | 6/1976 | Cayle et al. | 162/158 |
| 4,135,000 | 1/1979 | Schuldt, Jr. | 530/371 |
| 4,487,831 | 12/1984 | Day et al. | 435/99 |
| 4,562,150 | 12/1985 | Yamanabe et al. | 435/99 |
| 4,628,029 | 12/1986 | Eveleigh et al. | 435/99 |
| 5,006,472 | 4/1991 | Dove et al. | 435/270 |

OTHER PUBLICATIONS

Boehringer Mannheim Catalogue, 1985, pp. 30, 32–36 and 38–39.
Viikari et al., Process Biochem., 12(4), pp. 17–19, May 1977.
Oleson et al., Archives of Biochem. & Biophys., vol. 211, No. 1, pp. 478–484, 1981.
Oleson et al., Archives of Biochem. & Biophys., vol. 204, No. 1, pp. 361–370, 1980.

*Primary Examiner*—David M. Naff
*Assistant Examiner*—Michael V. Meller
*Attorney, Agent, or Firm*—Finnegan, Henderson, Farabow, Garrett & Dunner

[57] ABSTRACT

A method for degrading nucleic acids in a waste fermentation solution is disclosed. The method comprises exposing the waste solution to RNases and/or DNases released by autolysis of and/or secreted from *Paecilomyces lilaninus* which are present in or added to the waste solution. The fermentation of the microorganism occurs under sterile conditions. The microorganism can be transformed with nuclease-encoding genes and added to the waste solution before fermentation. The preferred strain of *Paecilomyces lilacinus* is DSM 5650.

7 Claims, 1 Drawing Sheet

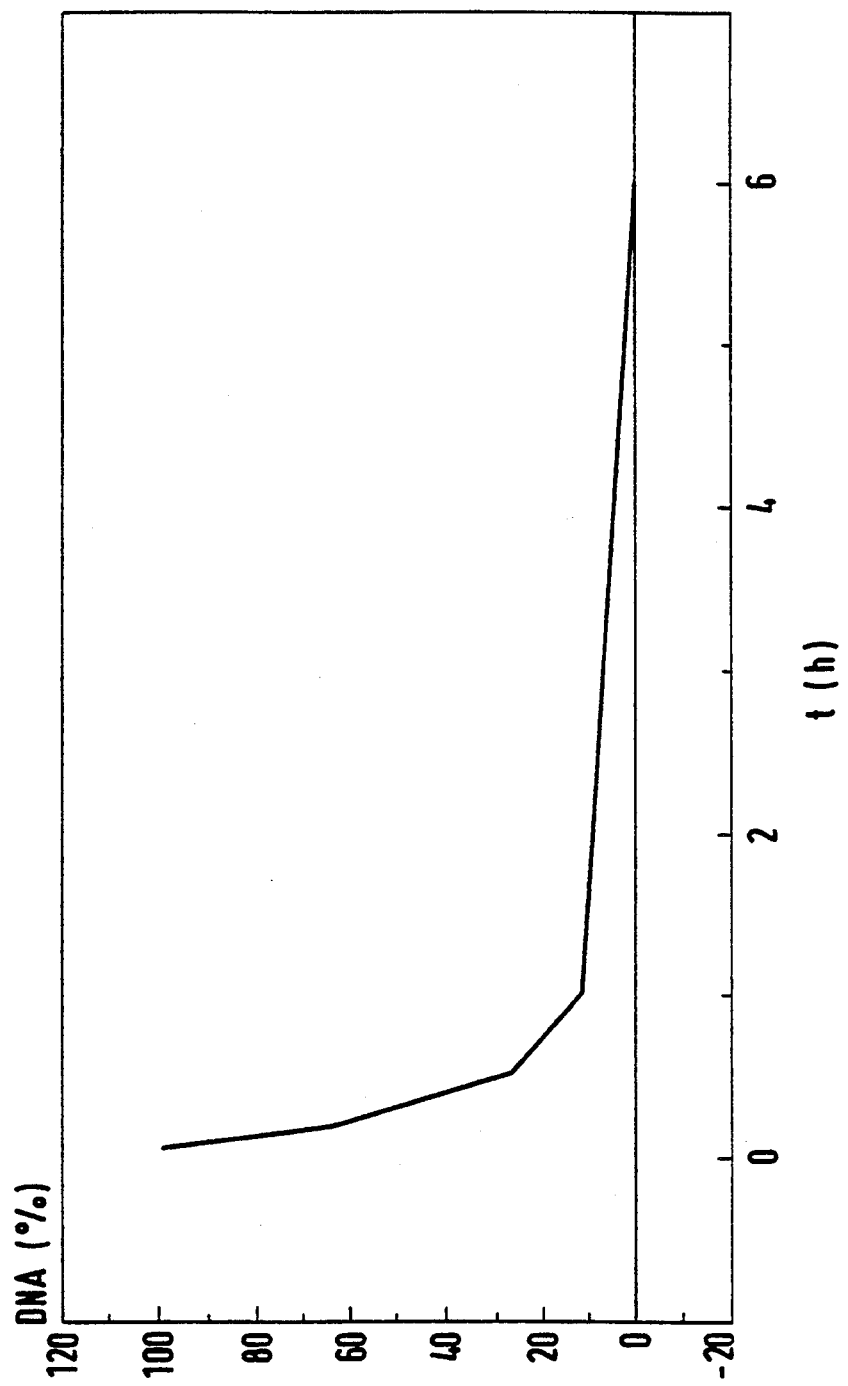

METHOD FOR DEGRADING NUCLEIC ACIDS IN WASTE FERMENTATION SOLUTIONS WITH *PAECILOMYCES LILACINUS*

This application is a continuation of application Ser. No. 619,449, filed Nov. 29, 1990, now abandoned.

The invention relates to methods for the biological inactivation of nucleic acids. The material which results from biotechnological production processes and which is contaminated with the genetically manipulated microorganisms used (residual fermentation broth, aqueous washings etc.) is collected in containers and broken down by autolysis and/or deliberate contamination with naturally occurring bacteria, yeasts or saprophytic fungi.

Biotechnological production processes are increasingly employed to obtain biological substances and active compounds (proteins, polysaccharides, antibiotics, amino acids, vitamins, alcohols inter alia). It is now possible by molecular biological techniques to produce proteins in heterologous organisms. In this connection, it is possible to express microbial, plant, animal and human genes in the other host cells in each case. Predominantly used nowadays for the synthesis of proteins are bacteria such as *Escherichia coli, Bacillus subtilis* and *Streptomyces lividans* and yeasts such as *Saccharomyces cerevisiae, Pichia pastoris* and *Kluyveromyces lactis*. However, animal cells (for example ovary cells of the Chinese hamster [CHO cells], mouse cells for example [C127i cells]) and human cells are also employed for heterologous gene expression. The production of the active compounds preferably takes place in fermenters because in these the synthesis can be controlled by modern control techniques. The products are either obtained from the cells or they are excreted into the culture broths.

It is common to all the production processes that large amounts of cell material result at the end and contain, inter alia, mainly natural and homologous nucleic acids (DNA and RNA) but also recombinant plasmid DNA or foreign DNA integrated into the genome of the host cell. It has hitherto been possible only with difficulty to estimate the possible risks on release of this recombinant DNA for the environment. Thus, on the precautionary principle, statutory requirements and regulations have been issued by authorities and institutions in most countries (such as, for example, in the Federal Republic of Germany the Central Committee for Biological Safety (ZKBS) of the Federal Board of Health in Berlin), which call for inactivation of the waste material, which is usually liquid, and thus of the amount of nucleic acids present after the production process as protection against a possible risk to the environment.

The nucleic acids can be inactivated physically, for example by heat. This is a process which requires a large quantity of energy and thus is a cost-intensive method. On the other hand, the nucleic acids can be inactivated chemically. Thus, for example, the Patent Application WO 89/03226 proposes a method by means of which DNA is inactivated chemically by heat treatment in the presence of percarboxylic acid, alkali metal peroxide or alkali metal peroxomonosulfate. A similar inactivation method is based on the use of citric acid. Both the latter method and other chemical methods have the disadvantage that they pose potential risks to the health of the users and/or the remaining final products are environmentally hazardous. In both methods the addition of the appropriate chemicals makes it possible to achieve complete inactivation of the nucleic acid even at relatively low temperature (for example 80° C.).

The invention now provides methods by which nucleic acids can be biologically inactivated at room temperature. These methods are efficient, cost-effective and environmentally acceptable. They are based on the breakdown of nucleic acids by specific enzymes (nucleases, i.e. DNases and RNases) and the formation of these enzymes by, inter alia, microorganisms which are present in or added to the culture broth or waste water.

The methodological steps drawn up here were carried out with fermentation broths and waste waters in which DNases—including recombinant DNA—can be released by lysis of animal cells.

In particular, a method in which the resulting material contaminated with nucleic acids (residual fermentation broth, cells, aqueous washings etc.) is collected in containers and deliberately incubated for some time at room temperature while stirring is described. The DNases which have passed into the container (for example release by cell lysis or microbial secretion) are able completely to break down DNA, including recombinant plasmid DNA, within a short time. Incomplete emptying of the waste-water collecting container means that the microbial populations retain their composition. They are able, when the container is refilled with waste water, to multiply further and excrete DNases when the waste water contains utilizable energy sources such as, for example, DNA.

Thus, recombinant, as well as host-specific, nucleic acids present in the waste water are completely broken down by nucleases, and no thermal or chemical inactivation of the waste water is necessary. It has also been found that the microorganisms do not take up recombinant DNA from the waste-water collecting container, and that the recombinant DNA, which would necessarily be stable in the waste water in the absence of the DNase activity, is neither expressed nor replicated in the abovementioned microorganisms.

The growth of the microorganisms which break down nucleic acids takes place even at room temperature and without the customary fermentation conditions such as oxygen input, stirring of the culture broth and other measures. Nevertheless, in order to increase the rate of growth of the microorganisms and to achieve higher cell densities, it is possible to ferment the waste water, for example even at temperatures which are above normal room temperature.

Microorganisms which have been isolated from the waste water and identified as DNAse excreters can also be multiplied outside the waste water and added in concentrated form to the waste water to increase the DNase activity before the incubation step.

It is furthermore possible for the genes which code for the secreted DNases also to be cloned and additionally expressed to the desired product so that even during the production process DNases are formed and excreted and break down free DNA in the culture broth and then in the waste water.

It is also possible to add isolated DNases to the waste water. In this procedure the DNases can be applied as free protein molecules or as immobilized enzymes coupled either to a separate carrier material or to the microcarriers, used for the cell fermentation themselves. Selection of the microbial flora intrinsic to the waste water ensures that a broad spectrum of DNases with different properties with regard to catalytic activity, half-life, substrate specificity, pH optimum and the like is present for breaking down nucleic acids.

The enzymatic breakdown of recombinant DNA by these newly developed methods has advantages over physical or chemical methods of nucleic acid inactivation. These methods dispense with agents which are unacceptable to the personnel using them and to the environment. They are considerably more cost-efficient, less labor-intensive, less susceptible to disturbance and are considerably more reliable in terms of worker protection than, for example, the inactivation of nucleic acids by heating, in particular by autoclaving. The microorganisms do not take up the recombinant DNA so that neither replication nor expression of the recombinant DNA occurs. The recombinant DNA is, on the contrary, completely metabolized, i.e. recombinant DNA is converted by this method into natural biomass whose microbial population composition does not essentially differ from the biomass in natural biotopes or clarification plants.

Accordingly, the invention relates to methods for inactivating nucleic acids, which comprise exposure to RNases and/or DNases released by autolysis and/or secretion. Preferred methods use nucleases released during fermentation under sterile conditions and/or nucleases released by microorganisms after fermentation under non-sterile conditions. Particularly preferred methods entail addition of purified nucleases or nuclease-releasing microorganisms, very particularly the saprophytic fungus AW13, deposited in accordance with the Budapest Treaty at the German Microorganism Collection under No. DSM 5650. The invention furthermore relates to the abovementioned saprophytic AW13 itself, identified as *Paecilomyces lilacinus*, including the other nuclease-excreting strains of this species.

The invention is furthermore contained in the examples and the patent claims.

EXAMPLES

The following examples relate to conventional production plants for recombinant human erythropoietin (EPO). The production plant based on the "classical" principle comprises a fermenter, a waste-water collecting container and a sterilizing plant. The cellular constituents and carrier material in the fermentation broths are separated by sedimentation. The supernatant is then drawn off and clarified by filtration. Moreover, the supernatant after the filtration is subjected to a purification process for obtaining human erythropoietin, while the solid constituents, that is to say cell and carrier residues with the filter are disposed of by incineration. Waste liquids from the purification process are passed into the waste-water collecting container. After drawing off the culture broth the cell and carrier sediment is flushed out with tap water and passed into the waste-water collecting container. The fermenter is then filled with tap water and heated to 120° C. for 20 minutes. After cooling to 80° C., this water is then likewise passed into the waste-water collecting container. Additional waste water resulting from further cleaning of the fermenter is likewise passed into the waste-water collecting container. The waste water in the waste-water collecting container is thus composed of waste water from the EPO purification process and from the cleaning of the fermenter. All the waste-water mixtures show conditions which are non-physiological for animal cells because of the use of tap water for cleaning the fermenter. Once the liquid in the waste-water collecting container has reached a particular level, the waste water is stirred for 30 minutes and then pumped into the kill tank In the kill tank plant the liquid is heated to 120° C. and kept at this temperature for 20 minutes. The inactivated waste water is then cooled to 80° C. and subsequently mixed with ten times the amount of tap water and discharged into the sewers.

EXAMPLE 1

Breakdown of DNA by DNases in the Supernatant From Cultured Animal Cells

During fermentation of animal cells there is continuous death of cells, which leads to release of nucleic acids and proteins. In production processes with recombinant DNA it is important to monitor the whereabouts of the recombinant DNA during and after the fermentation. We have found that the DNA content in culture supernatants from fermentation of the mouse cell line 3T1, which contains pCES plasmid DNA (see Patent Application EP-A-267 678) and produces EPO, is very low (<100 pg/ml). Further investigations have revealed that culture supernatants from fermentation of these cells contain DNase activity. The natural DNase activity is so high that complete breakdown of 10 µg of pCES DNA/ml in the culture supernatant is possible after incubation at room temperature for 6 hours (Fig.). This is why neither the pCES plasmid molecule which is 14.3 kb in size nor other smaller fragments of the plasmid are detectable by Southern blot hybridization even in culture supernatants.

EXAMPLE 2

Breakdown of DNA by DNases in Waste Water

All waste waters resulting from the fermentation plant mentioned in Example 1 are nowadays, because of the requirements of statute and authorities, collected in a waste-water collecting container and then autoclaved in the inactivation plant. This entails the collecting container being about 30% or more filled and then pumped every hour as a minimal time range into the sterilizing plant for autoclaving. The collecting container is, however, emptied only incompletely so that about 10–20% of the waste water remain. This waste water is then mixed with the new waste water which is introduced. DNA breakdown tests similar to those with the culture supernatants from the fermentation (see Example 1) were also carried out with samples from the waste-water collecting container. Once again, a DNase activity of at least 10 g of DNA/ml/6h was found in each case.

There is a drastic reduction in the transformability of 10 µg of plasmid DNA into competent *E. coli* bacteria ($2 \times 10^8$ clones/µg of DNA), which have been treated in this way and it can be completely eliminated, depending on the composition of the waste water (Tab.).

The DNase activity can be experimentally released from cells by treatment with tap water. This approximately corresponds to the conditions when the fermentation equipment is cleaned with tap water.

The DNase activity in the waste water can be inhibited in the presence of 10 mM EDTA. EDTA forms chelates to trap doubly charged ions which are essential for the biological activity of the DNases from the liquid. This is why care must be taken that the concentration of, for example, $Mg^{2+}$ and $Zn^{2+}$ is sufficient if EDTA is present.

Since small amounts of cell debris get into the waste water, DNA was isolated therefrom and analyzed. Even in the debris, where the DNA is relatively protected by cellular proteins, it was possible to detect only fragments but no intact pCES plasmid molecules.

EXAMPLE 3

Isolation of microorganism from waste water

Since the waste waters in the collecting container (see Example 2) are no longer sterile, the possibility of accumulation of microorganisms in the waste water was investigated. It was found that the organism count (colony-forming units) was $10^5$/ml on incubation in LB agar at 30° C.; the measurable organism count was $10^4$/ml on YPD agar and $10^3$ on YNB agar.

The organism counts in the container will certainly fluctuate after introduction of fresh waste water, but the values determined above show that the organic material in the waste water is sufficient to ensure, even under poor culture conditions (no agitation, no additional aeration) and despite addition of rinsing agents, a considerable multiplication of microorganisms.

It was investigated whether these microorganisms isolated from the waste water are able to take up and replicate recombinant DNA. No pCES plasmid or a fragment thereof was detectable by colony hybridization in any of the organisms.

Since recombinant nucleic acid is released by lysed mouse cells, it was now attempted to isolate from the waste water microorganisms which are able to excrete DNases.

Aliquots of 0.01, 0.05 and 0.1 ml of waste water were spread with a spatula on LB agar (mixture 1) and YPD agar (mixture 2) and incubated at 30° C. An attempt was also made at accumulating microorganisms with DNase activity from the waste water in a medium which has DNA almost exclusively as source of energy and carbon. The following medium was made up for this purpose:

| DNA medium: | |
| --- | --- |
| 0.1 g | of DNA from herring sperm |
| 19.0 ml | of tap water |
| 0.01 ml | of LB medium |
| 0.1 ml | of M9 10x salt solution |
| 0.01 ml | of 1 M CaCl$_2$ |
| 0.01 ml | of 1 M MgCl$_2$ |
| 0.01 ml | of 1 M (NH$_4$)$_2$SO$_4$ |
| 10 × M9 medium: | |
| 70 g | of Na$_2$HPO$_4$ × H$_2$O |
| 30 g | of KH$_2$PO$_4$ |
| 10 g | of NH$_4$Cl |
| | H$_2$O ad 1000 ml |
| LB medium: | |
| 10 g | of tryptone |
| 5 g | of yeast extract |
| 5 g | of NaCl |
| | H$_2$O ad 1000 ml |
| YPD medium: | |
| 20 g | of peptone |
| 10 g | of yeast extract |
| 20 g | of glucose |
| | H$_2$O ad 1000 ml |

This DNA medium was mixed with 1 ml of waste water and incubated at 30° C. for four days. The medium became cloudy and, under the microscope, various microorganisms were identified. Aliquots of 0.01 and 0.05 ml were removed from this mixture and spread on LB agar with a spatula (mixture 3). It was possible in all the mixtures to isolate microorganisms and take them in pure culture.

Mixture 1 (LB agar): AW1, AW2, AW3, AW4, AW5, AWS, AW9
Mixture 2 (YPD agar): AW10, AW11, AW12, AW13
Mixture 3 (DNA medium): AW6, AW7

EXAMPLE 4

Characterization of Seven Microorganisms Taken in Pure Culture

Thirteen microorganisms of different colony morphology and color were taken in pure culture. All of them grew on agar plates with YPD or LB medium. The isolate AW10, a mold with black aerial mycelium, was not investigated further because it did not grow in YPD and LB liquid cultures. The isolates AW1, AW2, AW4, AW6 and AW12 were discarded because, after initial investigations, they apparently do not excrete DNases on growth in various media. The isolate AW3 likewise secretes no DNases in liquid cultures, but was included in subsequent experiments as a negative control.

Description of the colonies of the isolates grown on LB agar:
AW3: yellowish coloration
AW5: colorless
AW6: fungal appearance, ragged margin, colony raised, beige-colored
AW7: white, glossy
AW8: orange-colored
AW11: beige-colored
AW13: white aerial mycelium, becoming gray after one week, growing over the entire plate (analysis on YPD medium in this case)

Description of the isolates grown in YPD medium at 30° C., under the light microscope:
AW3: bacterium, coccoid, cells aggregate to clusters
AW5: bacterium, coccoid, cells growing as Diplo- or Streptococci
AW6: yeast-like cells, circular to slightly oval, some forming small chains, also branched forms
AW7: bacterium, coccoid, growing in clusters, larger than AW3 and AW5
AW8: bacterium, coccoid to oval cells, growing in clusters
AW11: large yeast-like cells, circular, singly or in pairs, no branches
AW13: saprophytic fungus with white aerial mycelium on agar plates, branched mycelium, growing very densely in YPD

EXAMPLE 5

Detection of Secreted DNases 30 ml of LB medium or YPD medium were inoculated with eight of the isolates in 300 ml Erlenmeyer flasks and incubated at 30° C. and 120 rpm. After incubation for 70 hours, the cells were spun down, and the supernatant was tested for DNA activity.

| Experiment A: | |
| --- | --- |
| 0.08 ml | of culture supernatant |
| 0.01 ml | of buffer |
| | (500 mM Tris-HCl, pH 7.5; 50 mM MgCl$_2$) |
| 0.01 ml | of plasmid solution |
| | (1.74 mg/ml) |
| Experiment B: | |

-continued

| | |
|---|---|
| 0.08 ml | of culture supernatant |
| 0.01 ml | of buffer (500 mM Tris-HCl, pH 7.5; 50 mM MgCl$_2$) |
| 0.015 ml | of lambda DNA (0.5 mg/ml) |

0.03 ml samples were taken after 0, 6, 10 and 16 hours, mixed with 0.005 ml of STOP mix (100 mM EDTA, 20% sucrose, bromophenol blue as marker), frozen at −20° C. and then fractionated in a 0.8% agarose gel at 90 V in 3 hours (Experiment A). In Experiment B aliquots were taken for analysis after 0, 8 and 24 hours.

Extracellular DNase activity was detectable in culture supernatants from the isolates AW5, AW6, AW7, AW8, AW11 and AW13. In some cases the DNase activity differed when cultured on LB medium or YPD medium. Thus, for example, the isolate AW6 excreted more DNAses when cultured on YPD medium than when cultured on LB medium. By contrast, the isolate AW8 secreted more DNases when grown on LB medium. On the other hand, no DNase activity was detectable with the isolate AW3 when grown either in LB medium or in YPD medium under the stated experimental conditions; the highest DNase activity was detected with the isolate AW13 under the given conditions. In LB and YPD medium this organism copiously excreted DNase(s) which was (were) able to break down both circular plasmid DNA and linear lambda DNA completely in a short time.

EXAMPLE 6

Secretion of DNases by the isolate AW13 in Waste Water

The isolate AW13 produces DNases not only when grown in YPD and LB medium but also in the waste water resulting from the production of EPO.

300 ml of waste water were autoclaved at 121° C. for 20 minutes and inoculated with 50 μl of a 2-day old AW13 culture (grown in YPD). 1 ml of culture broth was removed after 24 hours and after 96 hours and was centrifuged, and the supernatant was tested for DNase activity with plasmid DNA and lambda DNA as substrate. The experimental design was as described in Example 5. Sampling took place after 0 hours, 3.5 hours and 7 hours. DNA was incubated in autoclaved waste water as control. Waste water in which AW13 had grown contained high DNase activities. Both plasmid and lambda DNA were degraded.

Transformation of 100 pg of DNA equivalents after incubation of 10 μg of pCES DNA at room temperature in waste waters from a fermentation plant for animal cells.

| Incubation conditions | Colonies counted on ampicillin plates Waste water sample (No.) | | | |
|---|---|---|---|---|
| | 1 | 2 | 3 | 4 |
| 1 minute without EDTA | 6100 | 13300 | 10800 | 9600 |
| 1 minute with EDTA | 6742 | 10020 | 9600 | 7200 |
| 6 hours without EDTA | 10 | 2 | 134 | 0 |
| 6 hours with EDTA | 6100 | 6000 | 9000 | 6100 |

10 μg samples of pCES plasmid DNA were added to 1 ml of waste water and incubated at room temperature with or without EDTA (2 mM) for 1 minute or 6 hours. Then 10 μl were removed and transformed into competent bacteria of the E. coli strain DH5. The various samples (1–4) correspond to waste water taken from the collecting container filled to different levels with waste water of different compositions.

Key to the Fig.:

10 μg samples of pCES DNA were incubated in 1 ml of waste water from the collecting container for various times. Then 10 μl were removed and fractionated on an agarose gel. The gel was blotted onto nitrocellulose and hybridized with a radiolabeled fragment of 800 base pairs (bp) from the pCES plasmid and exposed. The signals on the X-ray film were evaluated quantitatively and plotted against the incubation time.

We claim:

1. A method for degrading nucleic acids in a waste fermentation solution, which comprises exposing the waste solution to RNases and/or DNases released by autolysis of and/or secreted from *Paecilomyces lilacinus* present in or added to the waste solution, said RNases and/or DNases being present during fermentation of the waste solution under sterile conditions.

2. The method of claim 1, wherein the RNases and/or DNases are present in or added to the waste solution after fermentation of the waste solution under non-sterile conditions.

3. The method of claim 1, wherein the *Paecilomyces lilacinus* has been purified and multiplied externally prior to addition to the waste solution.

4. The method of claim 1 wherein the *Paecilomyces lilacinus* is DSM 5650.

5. The method of claim 1, wherein the RNases and/or DNases in the waste solution are purified.

6. The method of claim 5, wherein the purified RNases and/or DNases are immobilized on a carrier material.

7. The method of claim 6, wherein the RNases and/or DNases are contained as immobilized enzymes in microcarriers used for cell fermentation.

* * * * *

UNITED STATES PATENT AND TRADEMARK OFFICE
CERTIFICATE OF CORRECTION

PATENT NO. : 5,369,029
DATED : November 29, 1994
INVENTOR(S) : Michael Broeker et al It is certified that error appears in the above-indentified patent and that said Letters Patent is hereby corrected as shown below:

Item [57] Abstract: Line 6, change "lilaninus" to --lilacinus--.

Signed and Sealed this

Sixteenth Day of May, 1995

Attest:

BRUCE LEHMAN

Attesting Officer          Commissioner of Patents and Trademarks